(12) United States Patent
Chen et al.

(10) Patent No.: US 6,805,702 B1
(45) Date of Patent: Oct. 19, 2004

(54) HYBRID SLEEVE MATERIAL AND STRUCTURE

(75) Inventors: John J. Chen, Plymouth, MN (US); Daniel J. Horn, Shoreview, MN (US)

(73) Assignee: SciMed Life Systems, INC, Maple Grove, MN (US)

( * ) Notice: Subject to any disclaimer, the term of this patent is extended or adjusted under 35 U.S.C. 154(b) by 226 days.

(21) Appl. No.: 09/716,757

(22) Filed: Nov. 20, 2000

Related U.S. Application Data

(63) Continuation-in-part of application No. 09/668,496, filed on Sep. 22, 2000, now Pat. No. 6,554,841.

(51) Int. Cl.[7] .................................................. A61F 2/06
(52) U.S. Cl. ...................... 623/1.11; 623/1.12; 606/194
(58) Field of Search ............................... 623/1.11, 1.12, 623/1.23, 1.17; 606/180, 191, 192, 194, 195, 108; 604/103.03, 103.05, 171, 180, 263, 264, 523–527

(56) References Cited

U.S. PATENT DOCUMENTS

| | | | |
|---|---|---|---|
| 3,825,036 A | 7/1974 | Stent ........................... | 138/174 |
| 4,950,227 A | 8/1990 | Savin ........................... | 604/8 |
| 5,108,416 A | 4/1992 | Ryan et al. .................. | 606/194 |
| 5,403,341 A | 4/1995 | Solar ............................ | 606/198 |
| 5,456,674 A | 10/1995 | Bos .............................. | 604/280 |
| 5,693,085 A | 12/1997 | Buirge et al. ................. | 623/1 |
| 5,836,965 A | 11/1998 | Jendersee et al. ............ | 606/198 |
| 5,968,069 A | 10/1999 | Dusbabek et al. ........... | 606/194 |
| 5,976,120 A | 11/1999 | Chow et al. .................. | 604/525 |
| 5,980,530 A * | 11/1999 | Willard et al. ................ | 606/195 |
| 6,183,505 B1 | 2/2001 | Mohn, Jr. et al. ........... | 623/1.11 |
| 6,221,097 B1 | 4/2001 | Wang et al. .................. | 623/1.11 |
| 6,331,186 B1 * | 12/2001 | Wang et al. .................. | 623/1.11 |

OTHER PUBLICATIONS

U.S. patent application Ser. No. 09/664,267, Dicaprio et al., filed Sep. 18, 2000.
U.S. patent application Ser. No. 09/664,268, Hanson, filed Sep. 18, 2000.
U.S. patent application Ser. No. 09/549,286, Gerberding et al., filed Apr. 14, 2000.
U.S. patent application Ser. No. 09/407,836, Wang et al., filed Sep. 28, 1999.

* cited by examiner

Primary Examiner—Corrine McDermott
Assistant Examiner—Urmi Chattopadhyay
(74) Attorney, Agent, or Firm—Vidas, Arrett & Steinkraus, P.A.

(57) ABSTRACT

A stent delivery system comprising a catheter including a stent mounting region. A stent disposed about the stent mounting region of the catheter, the stent having a distal end and a proximal end, the stent further having an unexpanded state and an expanded state. At least one stent retaining sleeve having a first end overlying an end of the stent when the stent is in the unexpanded state, a second end engaged to at least a portion of the catheter adjacent to the stent mounting region. The outside surface of the stent retaining sleeve being composed of a first material, at least a portion of the first end of the inside surface being composed of a second material. The first material having a first predetermined hardness, the second material having a second predetermined hardness, the second predetermined hardness having a higher durometer value than the first predetermined hardness.

11 Claims, 4 Drawing Sheets

HYBRID SLEEVE MATERIAL AND STRUCTURE

CROSS-REFERENCE TO RELATED APPLICATIONS

This application is a Continuation-In-Part application from U.S. application Ser. No. 09/668,496, filed Sep. 22, 2000, now U.S. Pat. No. 6,554,841 the entire contents of which is hereby incorporated by reference.

STATEMENT REGARDING FEDERALLY SPONSORED RESEARCH

Not Applicable

BACKGROUND OF THE INVENTION

1. Field of the Invention

This invention relates to medical device delivery catheters in general, and specifically to balloon catheters for use in delivering a medical device such as a stent to a desired body location, such as in a blood vessel. More specifically, this invention relates to socks or sleeves used in retaining the stent in the unexpanded state which have reduced frictional engagement with the ends of a stent and/or balloon cones. In the present invention such reduced frictional interaction is made possible by providing the sleeve or sleeves with an inside surface of which at least a portion is characterized as being harder than the outside surface.

2. Description of the Related Art

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents may be crimped to their reduced diameter about the delivery catheter, maneuvered to the deployment site, and expanded to the vessel diameter by fluid inflation of a balloon positioned on the delivery catheter. The present invention is particularly concerned with delivery and deployment of inflation expandable stents, although it is generally applicable to self-expanding stents when used with balloon catheters.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al, relates to an expandable stent delivery system in which a sleeve overlaps the distal or proximal margin (or both) of the stent during delivery. That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion(s) of the stent to hold it in place on the catheter in a contracted condition. Each sleeve is elastomeric in nature so as to stretch and release the stent when it expands for implantation. The stent is expandable by means of the expandable balloon on the catheter. During expansion of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Copending U.S. patent application Ser. No. 09/407,836 which was filed on Sep. 28, 1999 and entitled *Stent Securement Sleeves and Optional Coatings and Methods of Use*, and which is incorporated in its entirety herein by reference, also provides for a stent delivery system having sleeves. In 09/407,836 the sleeves may be made up of a combination of polytetrafluoroethylene (PTFE) as well as one or more thermoplastic elastomers. Other references exist which disclose a variety of stent retaining sleeves.

A common problem which occurs in catheter assemblies is friction or adhesion between various parts which periodically come into contact with one another during the medical procedure. For instance, friction can occur between the guide catheter and guide wire, between the introducer sheath and the guide catheter, or between the guide catheter and the balloon catheter, for instance, and may increase the difficulty of insertion, cause loss of catheter placement, and result in discomfort to the patient or damage to the vasculature. In catheters equipped with stent retaining socks or sleeves, friction between the balloon and sleeve, and/or the stent and sleeve may also cause retraction of the sleeves to be made more difficult. In stent delivery systems where the stent employs a relatively soft coating material on it surface, such as a drug carrier, the relatively soft coating may increase its friction to the sock or sleeve system. An example of which may be seen in U.S. Pat. No. 5,693,085 to Buirge et al., the entire contents of which is incorporated herein by reference.

It is therefore desirable to reduce the friction due to the sliding between the various parts of the catheter assemblies. Copending U.S. application Ser. No. 09/549,286 which was filed Apr. 14, 2000 describes a reduced columnar strength stent retaining sleeve having a plurality of holes. The relatively reduced columnar and radial strength provided by the holes allows the sleeve to be retracted off of a stent without the need for lubricant.

Lubricants however may be used in a variety of stent delivery catheters. Many lubricants and lubricious coatings types have been used in conjunction with balloon catheters. Both hydrophilic and hydrophobic coatings and lubricants are well known in the catheter art. For example: copending U.S. patent application Ser. No. 09/407,836 which was filed on Sep. 28, 1999 and entitled Stent Securement Sleeves and Optional Coatings and Methods of Use, provides for a stent delivery system having sleeves. In Ser. No. 09/407,836 the sleeves may be made up of a combination of polytetrafluoroethylene (hereinafter PTFE) as well as one or more thermoplastic elastomers. Copending U.S. patent application Ser. No. 09/427,805 filed Oct. 27, 1999, and entitled End Sleeve Coating for Stent Delivery, describes the use of stent retaining sleeves having lubricious coatings applied thereto.

Copending U.S. patent application Ser. No. 09/273,520 filed Mar. 22, 1999, entitled Lubricated Sleeve Material For Stent Delivery likewise describes the use of stent retaining sleeves and lubricants.

Stent delivery systems which may not require the use of lubricants have been proposed, such as copending U.S. application Ser. No. 09/549,286 mentioned above. Another example of a stent delivery system and retaining sleeve which may not require lubrication is Copending application Ser. No. 09/668,496 filed Sep. 22, 2000 and entitled Striped Sleeve For Stent Delivery describes a two component sleeve having one or more substantially longitudinally oriented stripe of a hard material and a softer material. The striped configuration of materials in the sleeve allows the sleeve to radially expand but with limited or no longitudinal expansion. The unique expansion characteristics provided by the striped configuration helps avoid a need to use a lubricant with the sleeve, though a lubricant may still be utilized therewith if desired.

The entire content of all patents and applications listed within the present patent application are incorporated herein by reference.

BRIEF SUMMARY OF THE INVENTION

The instant invention is directed to a medical device delivery system comprising a catheter assembly having a medical device receiving region and at least one retaining sleeve for retaining the medical device on the receiving region prior to delivery. An expandable medical device, such as a stent, is disposed about the medical device receiving region of the catheter assembly. At least one retaining sleeve is disposed about an end of the expandable medical device and at least a portion of the catheter assembly.

The at least one retaining sleeve further comprises an inside surface and an outside surface. The outside surface being comprised of a first material and at least the portion of the inside surface which is constructed to overlay a stent being comprised of a second material. The first and second materials having different harnesses, the second material being harder than the first. As is known, for most polymer materials, the hardness represents the capacity of elongation when the polymer is exposed to an outside acting force, this is especially true for elastomeric materials (e.g. the lower a material's hardness the higher the material's elasticity).

Unlike the Ser. No. 09/668,496 application, from which the present application depends, and which provides for a sleeve having reduced longitudinal elongation, the present invention improves sleeve retractability by providing at least the portion of the inside surface of the sleeve which may overlay a stent with a material which has a greater hardness than the majority of the sleeve material. Such a relatively hard material preferably provides the sleeve with a surface having lower frictional engagement to the stent.

In an embodiment of the invention the first material and second material are co-extruded polymers.

In an embodiment of the invention the second material is a coating on the first material.

In an embodiment of the invention the inside surface is comprised entirely of the second material.

In an embodiment of the invention only the portion of the inside surface which is constructed and arranged to overlay a stent is comprised of the harder material.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
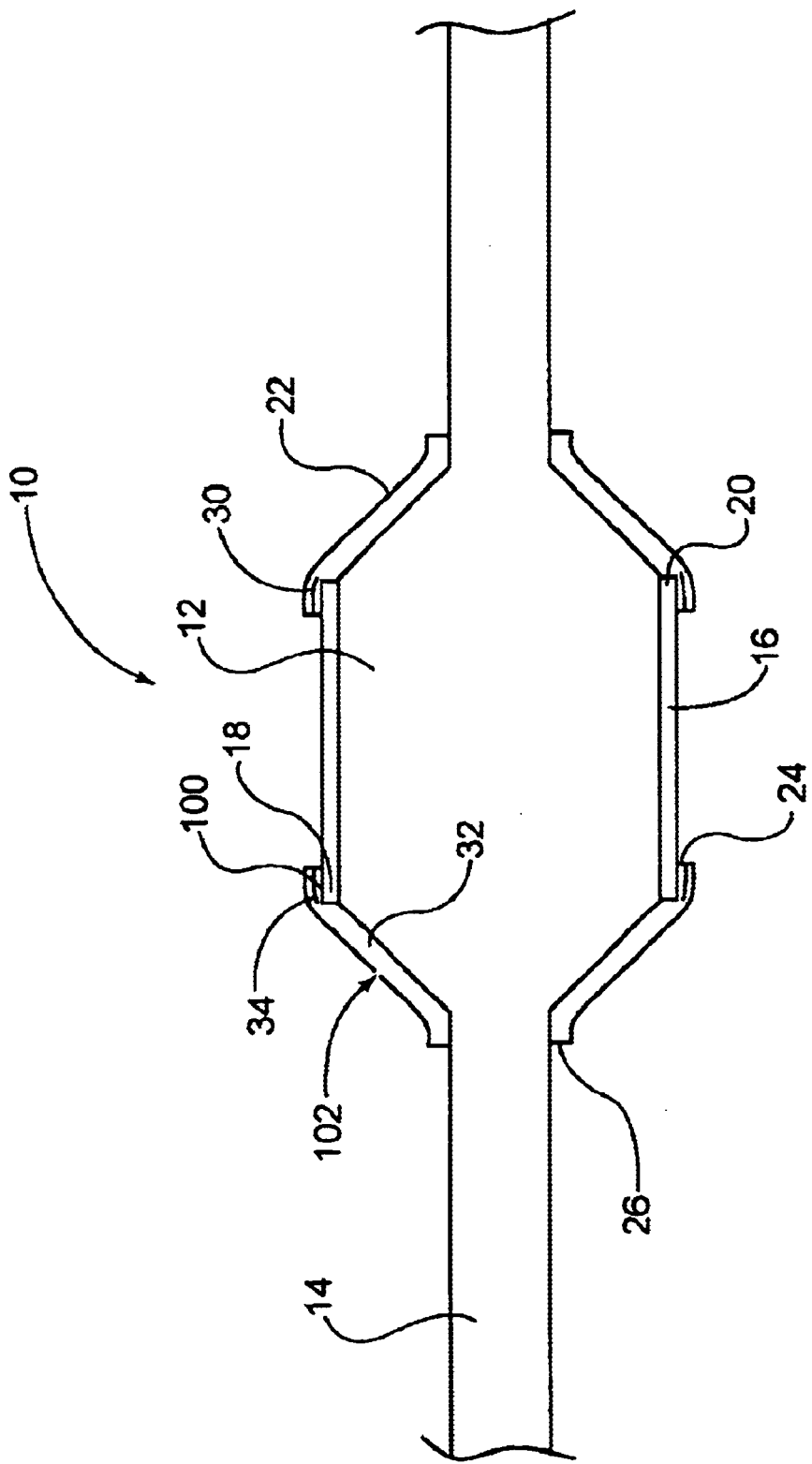
FIG. 1 is a side view of a first embodiment of the invention.

As may be seen in FIG. 1, the present invention may be embodied in a stent delivery catheter, indicated generally at 10. Catheter 10, includes a stent mounting region 12, the stent mounting region 12 may be an inflatable portion of the catheter or may be a separate balloon mounted to the catheter shaft 14. The balloon 12 may have an unexpanded state and an expanded state. A stent 16, disposed about the stent mounting region 12 may be delivered when the balloon 12 is expanded to the expanded state.

The stent 16 includes a proximal end 18 and a distal end 20. In the embodiment shown a stent retaining sleeve 22 overlies at least a portion of each end 18 and 20. As is known in the art, when the balloon 12 and stent 16 are expanded to their expanded state, the ends of the stent retaining sleeves 22 are configured to retract off of the stent ends 18 and 20. In the present invention, the sleeves 22 have a unique construction which provides the first portion 24 of the sleeve which overlies the stent 16, with a reduced frictional engagement with the stent 16 by providing the inside surface 100 of the first portion 24 with a material 34 which is harder than that of the outer surface 102 of the sleeve 22.

The second portion 26 of the sleeve 22 is disposed about and is engaged to a portion of the catheter shaft 14 adjacent to the balloon 12.

As stent 16 is expanded, the stent ends 18 and 20 will eventually be drawn from underneath the stent retaining sleeves 22. By providing a sleeve 22 which has a reduced frictional engagement with the stent ends 18 and 20 the present invention ensures that the stent is delivered with improved sleeve retractability.

As previously indicated, the sleeves 22 are constructed from at least two materials having different hardness characteristics. The first material 30 is formed into a generally tubular body 32 which provides the sleeve with its shape as well as its outer surface 102. At least a portion of the first end 24 of the inside surface 100 is composed of the second material 34.

The first material 30 may be any elastic material known which has a hardness as measured by a Shore durometer of less than 55 D. Preferably the durometer hardness of the first material is between 40A and 100A. The second material 34 may be any material having a durometer hardness greater than about 55 D. In at least one embodiment of the invention the first material 30 has a hardness of 35D and the second material 34 has a hardness of 70D.

The first material 30 may be selected from one or more of the following substances: soft grade polyester/polyether elastomers such as Arnitel™ available from DSM Engineering, polyurethane-polyether polymers, such as Tecothane™ 1074A available from Thermedics, Inc.; polyester-polyurethanes, such as Pellethane™ 2102-75A sold by Dow Chemical; polyester-polyurethanes, such as Estane™ 5703P sold by BF Goodrich; polyether block amides, such as Pebax™ 2533 available from Elf Atochem; and styrene-butadien-styrene triblock copolymers such as Kraton™ D1101 sold by Shell Chemical company. Other materials which may also be used in the production of the first material 30 include, but are not limited to styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, soft block copolymers, and any combinations thereof.

The second material 34 may be selected from one or more of the following substances: polyethyleneterephthalate (PET), polybutylene terephthalate (PBT), polytrimethylene terephthalate (PTT),Nylon™, engineering thermoplastic polyurethanes, fluoropolymers, polyester/polyether elastomers such as Arnitel™ available from DSM Engineering, polyurethane-polyether polymers, such as Tecothane™1055D or 1075D both of which are available from Thermedics, Inc.; polyester-polyurethanes, such as Estane™58170 sold by BF Goodrich; polyether block amides, such as Pebax™7233 or 6333 both of which are available from Elf Atochem. Other materials which may also be used in the production of the second material 34 include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyarnides, polyphenylene sulfide, polyarylethersulfones, polyaryletherketones, polytetrafiuoroethylene, and any combinations thereof.

The above examples of the first and second materials 30 and 34 are in no way exhaustive of the potential substances or combinations of substances which may be used. The present invention is directed to a sleeve composed of any materials which have the hardness qualities previously described for the respective materials 30 and 34.

As may be seen in the various figures, the present invention may be embodied in a variety of manners. For instance, in the embodiment shown in FIG. 1 the catheter 10 is seen with a pair of sleeves 22 each of which have a first portion 24 with an inner surface 100 which is composed of a second material 34, such as is described above. Second material 34 may be a coating of hardened material applied to the inside surface 100 of the sleeve 22. Alternatively, the material 34 may be bonded or welded to the sleeve 22, or first material 30 and second material 34 may have been co-extruded together in the form of sleeve 22 shown. Other methods for joining the materials 30 and 34, such as selective coating by printing, may also be utilized.

Figure 2:
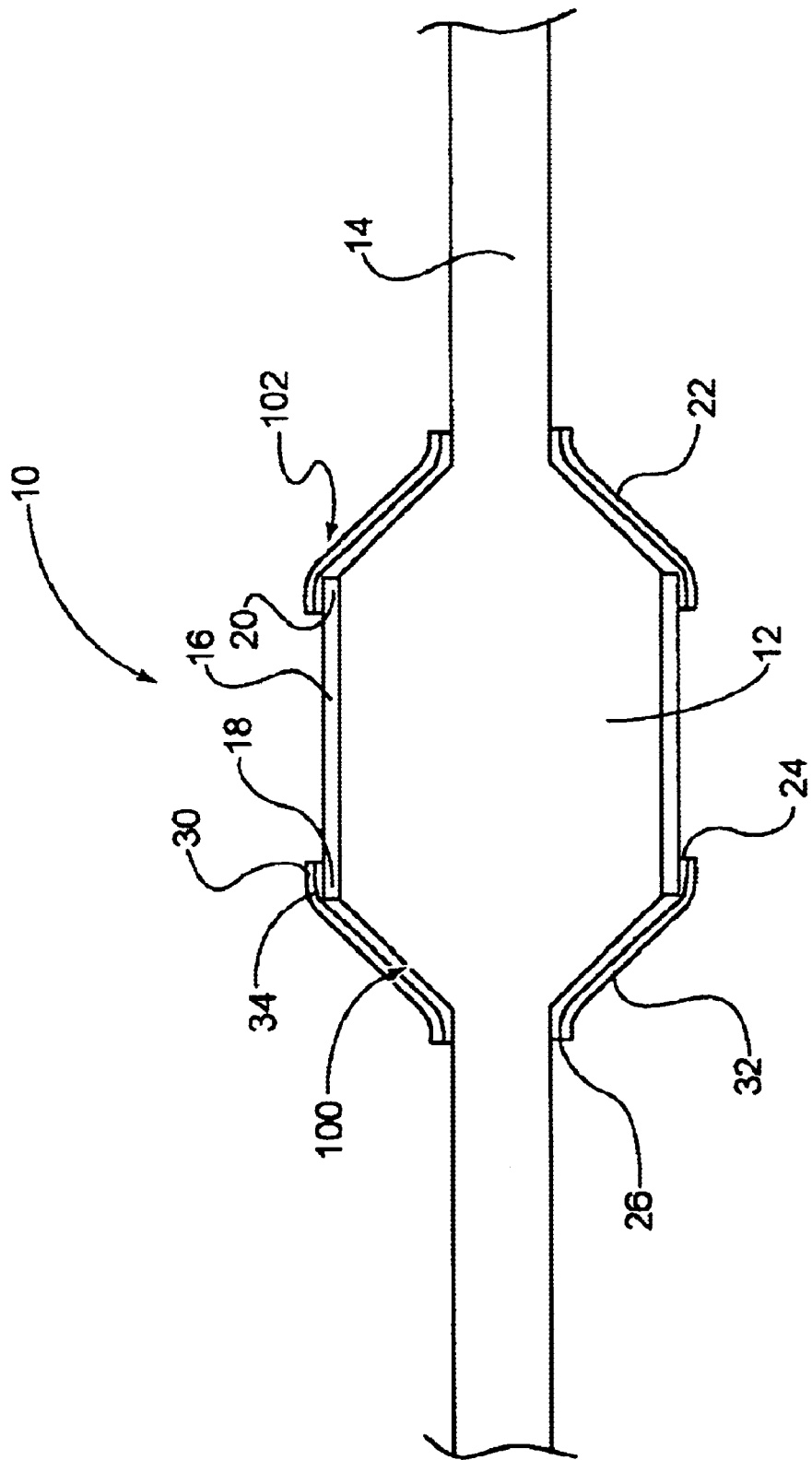
FIG. 2 is a side view of a second embodiment of the invention.

As may be seen in FIG. 2, the entire inside surface 100 of the sleeve(s) 22 may be composed of the second material 34.

Figure 3:
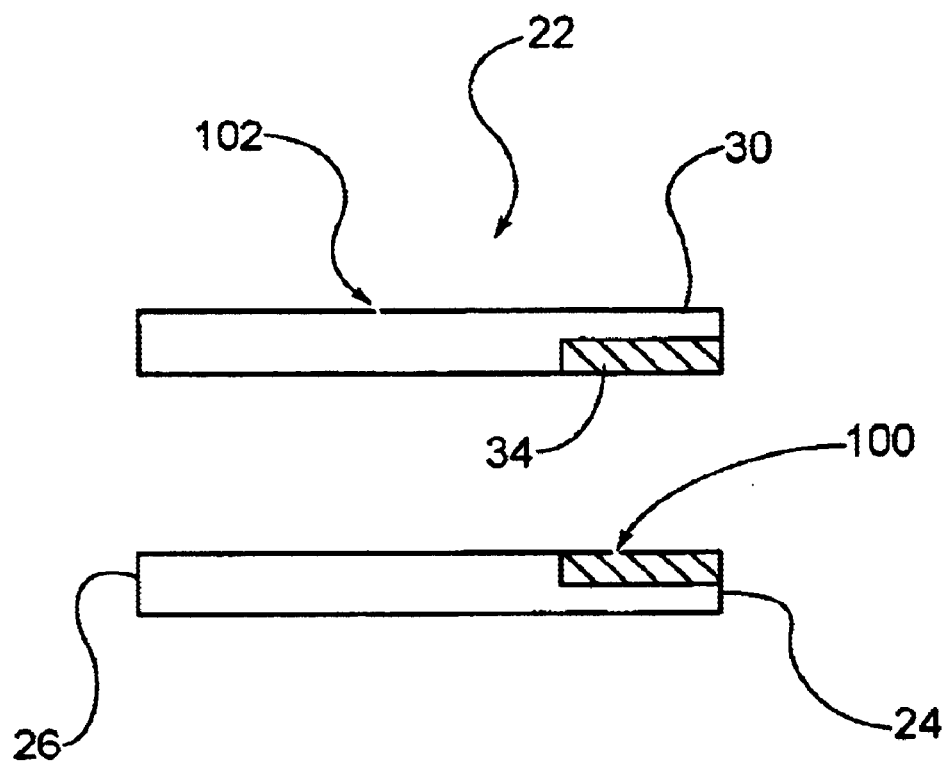
FIG. 3 is a side view of a third embodiment of the invention.
Figure 4:
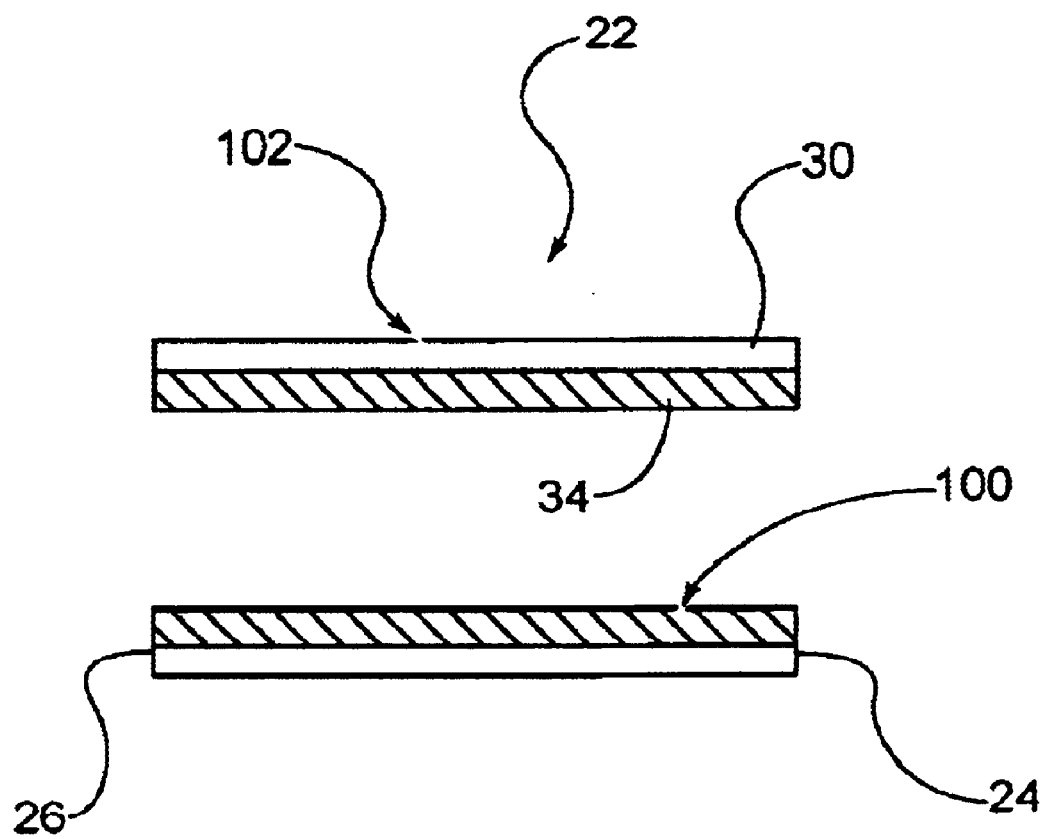
FIG. 4 is a side view of a forth embodiment of the invention.

FIGS. 3 and 4 show the sleeve configurations respectfully described in relation to FIGS. 1 and 2 as they may be embodied on a sleeve 22 exclusive of the stent delivery catheter 10.

In alternative embodiments, notably those utilized specifically for delivery of a self expanding stent, a retractable sheath (not shown) such as are known in the art, may be employed to overlay the stent. In such embodiments a single sleeve or two sleeves such have been shown and described may be employed to retain the self-expanding stent in place. When the sheath is retracted the stent will expand causing the sleeve(s) to retract.

The second material may also be relatively smoother than the first material.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery system comprising:
    a catheter including a stent mounting region;
    a stent disposed about the stent mounting region of the catheter, the stent having a distal end and a proximal end, the stent further having an unexpanded state and an expanded state, and
    at least one stent retaining sleeve, the at least one stent retaining sleeve having an inside surface and an outside surface and a first end and a second end,
        the first end overlying an end of the stent when the stent is in the unexpanded state, the second end engaged to at least a portion of the catheter adjacent to the stent mounting region;
        the outside surface consisting of a first material, and the inside surface consisting of a second material;
        the first material having a first predetermined hardness, the second material having a second predetermined hardness, the second predetermined hardness having a higher durometer value than the first predetermined hardness.

2. The stent delivery catheter of claim 1 wherein the second material is smoother than the first material.

3. The stent delivery catheter of claim 1 wherein the first predetermined hardness is less than approximately 55 D, and the second predetermined hardness is at least 55 D.

4. The stent delivery catheter of claim 1 wherein the first prdetermined hardness is approximately 35 D, and the second predetermined hardness is approximately 55 D.

5. The stent delivery catheter of claim 1 wherein the second material is a coating, the coating being applied to the inside surface of the at least one stent retaining sleeve.

6. The stent delivery system of claim 5 wherein the coating is selected from at least one member of the group consisting of: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof.

7. The stent delivery system of claim 1 wherein the first material is constructed from at least one member of the group consisting of: styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, polyester elastomers, polyamide elastomers and any combination thereof.

8. The stent delivery system of claim 1 wherein the second material is constructed from at least one member of the group consisting of: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal polyethers, polycarbonates, polyamides, polyphenylene sulfide, polyarylethersulfones, polyaryletherketones, polytetrafluoroethylene, and any combination thereof.

9. A stent delivery system comprising:
   a catheter including a stent mounting region;
   a stent disposed about the stent mounting region of the catheter, the stent having a distal end and a proximal end, the stent further having an unexpanded state and an expanded state, and
   at least one stent retaining sleeve, the at least one stent retaining sleeve having an inside surface and an outside surface and a first end and a second end,
   the first end overlying an end of the stent when the stent is in the unexpanded state, the second end engaged to at least a portion of the catheter adjacent to the stent mounting region;
   the outside surface being composed of a first material, at least a portion of the first end of the inside surface being composed of a second material;
   the first material having a first predetermined hardness, the second material having a second predetermined hardness, the second predetermined hardness having a higher durometer value than the first predetermined hardness wherein the first material and the second material are co-extruded.

10. A stent retaining sleeve for retaining stent ends on a balloon catheter comprising:
   a first material and a second material, wherein the first material has a first predetermined hardness and the second material has a second predetermined hardness, the second predetermined hardness being greater than the first predetermined hardness;
   the stent retaining sleeve having an inside surface and an outside surface, and a first end and a second end, the inside surface of the first end constructed and arranged to overlay an end of a stent, the second end constructed and arranged to be in contact with at least a portion of a catheter;
   the inside surface consisting of the second material.

11. A stent delivery system comprising:
   a catheter including a stent mounting region;
   a stent disposed about the stent mounting region of the catheter, the stent having a distal end and a proximal end, the stent further having an unexpanded state and an expanded state, and
   at least one stent retaining sleeve, the at least one stent retaining sleeve having a first end and a second end, the first end overlying an end of the stent when the stent is in the unexpanded state, the second end engaged to at least a portion of the catheter adjacent to the stent mounting region;
   the at least one sleeve having an inside surface and an outside surface, the entire inside surface being harder than the outside surface.

* * * * *